United States Patent
Shu et al.

[19]

[11] Patent Number: 5,948,019
[45] Date of Patent: Sep. 7, 1999

[54] HEART VALVE SUTURING RING WITH SURFACE COATING TO INHIBIT TISSUE INGROWTH

[75] Inventors: Mark C. Shu, Irvine; Hong S. Shim, Santa Ana, both of Calif.

[73] Assignee: Medtronic, Inc., Minneapolis, Minn.

[21] Appl. No.: 08/547,854

[22] Filed: Oct. 25, 1995

[51] Int. Cl.⁶ .................................. A61F 2/24; A61F 2/06
[52] U.S. Cl. ........................................... 623/2; 623/1
[58] Field of Search ................................ 623/1, 2, 11, 66, 623/3, 12, 900; 606/151, 154; 137/375, 527, 533.19, 862, 855, 858; 427/2.24, 2.25

[56] References Cited

U.S. PATENT DOCUMENTS

| | | |
|---|---|---|
| 4,197,593 | 4/1980 | Kaster . |
| 4,217,665 | 8/1980 | Bex . |
| 4,556,996 | 12/1985 | Wallace . |
| 4,790,843 | 12/1988 | Carpentier . |
| 4,936,846 | 6/1990 | Dureau ........................................... 623/2 |
| 4,979,959 | 12/1990 | Guire ........................................... 623/1 |
| 5,084,064 | 1/1992 | Barak et al. ................................. 623/1 |
| 5,098,877 | 3/1992 | Frautschi et al. .......................... 623/11 |
| 5,178,633 | 1/1993 | Peters . |
| 5,423,886 | 6/1995 | Arru et al. ................................... 623/1 |

FOREIGN PATENT DOCUMENTS

| | | |
|---|---|---|
| 0155245 | 9/1985 | European Pat. Off. . |
| 1093599 | 12/1967 | United Kingdom . |
| 8900841 | 2/1989 | WIPO . |

*Primary Examiner*—Michael J. Milano
*Attorney, Agent, or Firm*—Reed A. Duthler; Harold R. Patton

[57] ABSTRACT

An implantable prosthetic heart valve with a suturing ring having an impermeable or semi-impermeable coating over at least a portion of the surface thereof to prevent tissue ingrowth in the coated area or areas. The suturing ring is formed of a biocompatible fabric tube of a mesh weave having interstices permeable to tissue ingrowth and first and second axial ends fastened into a torus shaped, suturing ring body having an interior directed minor surface adapted to be fitted against the exterior annular wall of a valve body and an outward directed major surface. An upper ring shaped surface is formed adjacent the upper edge of the valve body and a lower ring shaped surface adjacent the lower edge of the valve body. The intermediate band is intended to be sutured into contact with the heart tissue orifice. First and second impermeable layer of biocompatible material fill the interstices of the mesh weave in the upper and lower ring shaped surface area. A smooth transition is formed at the junction of the suturing ring with the valve body by filling the gaps at the suturing ring/valve body juncture with the same or similar type of blood compatible material.

20 Claims, 2 Drawing Sheets

HEART VALVE SUTURING RING WITH SURFACE COATING TO INHIBIT TISSUE INGROWTH

FIELD OF THE INVENTION

The present invention generally relates to an implantable prosthetic heart valve suturing ring and particularly to a suturing ring having an impermeable or semi-impermeable coating over at least a portion of the surface thereof to prevent tissue ingrowth in the coated area.

BACKGROUND OF THE INVENTION

Implantable prosthetic heart valves are typically formed of an annular mechanical valve seat in a valve body and one or more occluding disks or leaflets that are movable between a closed, seated position and an open position in a prescribed range of motion. Prosthetic mechanical heart valves may be formed of blood compatible, non-thrombogenic materials, typically comprising pyrolytic carbon and titanium with hinge mechanisms and/or pivoting guides prescribing the range of motion of the disk or leaflets. Prosthetic tissue valves are formed from treated integral swine valve leaflets and valve annulus structure mounted to an annular valve body.

Such prosthetic heart valves are commonly provided with a suturing ring surrounding the valve body that is sewed by the surgeon to the peripheral tissue of a natural heart valve orifice after surgical removal of damaged or diseased natural valve structure. The suturing ring and valve body are typically fabricated so that they may be rotated with respect to one another by the application of force. Following implantation, the surgeon may desire to adjust the valve leaflet or disk orientation by rotation of the valve body within the suturing ring so that the valve mechanism can properly operate without interference from the surrounding heart tissue. Adjustment by rotation of the valve body requires a rotational force sufficiently small as to avoid damage to the sutured heart tissue or loosening of the sutures, and yet sufficiently great so that the valve, when properly positioned, does not further rotate during its long term operation.

The outer fabric layer of the typical suturing ring of the type shown in U.S. Pat. Nos. 4,197,593, 4,790,843, and 5,178,633 is porous and tear resistant so that needles and sutures pass through it when the suturing ring is sutured in place. Clinical studies indicate that a type of fibrous tissue forms on the suturing ring fabric layer as a result of the initial deposition of thrombus and its subsequent organization into avascular, that is tissue without vascularization, fibrous tissue. Normally, this is not a clinical problem, and the thin layer tissue formation and shallow growth into the fabric weave interstices is viewed as a positive factor in the stabilization of the suturing ring. Sometimes, however, a thick, vascular fibrous tissue is evolved through granulation tissue and the growth of capillaries in it. This type of fibrous tissue not only extends into the interstices of suturing ring fabric but also covers the suturing ring, and may produce procoagulant activity. More significantly, this type of vascular fibrous tissue often becomes excessively thicken as it continues to grow over the margin of the suturing ring and intrudes into the valve's annular opening and interferes with the range of motion of the leaflets or disk. This excessive growth is referred to in the literature as "pannus" overgrowth.

A thin carbon film coating of Biolite® carbon coating has been applied on some certain heart valve suturing rings, e.g., on the suturing rings of the Omnicarbon® valve and the Bjork-Shiley® valve. This kind of coating does not create an impermeable or semi-impermeable surface and does not reduce the surface porosity of a suturing ring, but is claimed to increase biocompatibility. Tissue ingrowth into the Biolite® coated, fabric interstices is intended and occurs.

It is desirable that a suturing ring for an artificial heart valve be provided that inhibits or minimizes tissue ingrowth into the valve annular opening yet acts to stabilize the valve suturing ring.

SUMMARY OF THE INVENTION

It is therefore an object of the present invention to provide a suturing ring for an artificial heart valve that inhibits or minimizes tissue ingrowth into the annular valve opening yet acts to stabilize the valve suturing ring.

A first aspect of the present invention encompasses the creation of an impermeable or semi-impermeable, blood compatible surface coating on a portion or portions of the suturing ring of a prosthetic heart valve in closest proximity to the valve body. The suturing ring is otherwise constructed in the conventional manner of an exposed, porous fabric layer to encourage tissue ingrowth and vascular tissue formation at a distance from the valve body, orifice and leaflets.

In particular, the suturing ring is formed of a biocompatible fabric tube of a mesh weave having interstices permeable to tissue ingrowth and first and second axial ends fastened into a torus shaped, suturing ring body having an interior directed minor surface adapted to be fitted against the exterior annular wall of a valve body and an outward directed major surface, means for fitting the interior directed surface of the annular shaped suturing ring body against the exterior annular wall leaving the outward directed major surface exposed with an upper ring shaped surface adjacent the upper end of the valve body and a lower ring shaped surface adjacent the lower end of the valve body and an intermediate band for being sutured against heart tissue in attachment of the suturing ring to a heart tissue orifice. A first impermeable layer of biocompatible material fills the interstices of the mesh weave in the upper ring shaped surface area, and a second impermeable layer of biocompatible material fills the interstices of the mesh weave in the lower ring shaped surface area.

A second aspect of the present invention is to provide a smooth transition at the juncture of the suturing ring with the valve body. The smooth transition is achieved by filling the gaps at the suturing ring/valve body juncture with the same or similar type of blood compatible material. It is theorized that this modification will eliminate homeostasis or flow stagnation regions at the gap leading to reduction in thrombus formation adjacent to the valve body.

The impermeable or semi-impermeable surface coating in the specified limited regions reduces or eliminates the interstices of the fabric layer, and consequently the porosity, of the suturing ring surface. The resulting suturing ring surface is smoother and more blood compatible, and is anticipated to result in less thrombus formation than would otherwise occur on the un-coated fabric layer and less chance for tissue granulation and capillary growth leading to the growth of vascular tissue into the heart valve orifice.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

For purposes of the present invention, it will be understood that the term "impermeable" encompasses the terms semi-permeable or semi-impermeable as used heretofore insofar as the latter suggest a degree of permeability to gases or liquids. The coating thicknesses of the impermeable coating bands and strips described below and the degree of permeability of the resulting coated fabric to gases and liquids under conditions encountered in the heart are selectable by those of skill in the art among those that are effective in decreasing growth of vascularized tissue that forms with tissue ingrowth into the open fabric weave interstices.

The present invention may be practiced in a number of embodiments in improving conventional suturing rings for prosthetic mechanical and tissue heart valves. It will be understood that the instant invention is not limited to any particular operating valve structure and indeed is applicable to ball-and-cage valves, floating disc valves, valves with multiple flaps or closures, and the like. All of these valves, however, are characterized by having an annular valve body carrying a circumferential suturing ring permitting the valve to be sutured to the heart tissue orifice left open after removal of a patient's diseased heart valve. The following description illustrates the practice of the invention in one preferred embodiment of a suturing ring mounted on a mechanical heart valve body of the type described in the above-referenced '593 patent, incorporated herein by reference, and commercially employed in the Medtronic® Hall heart valve.

Figure 1:
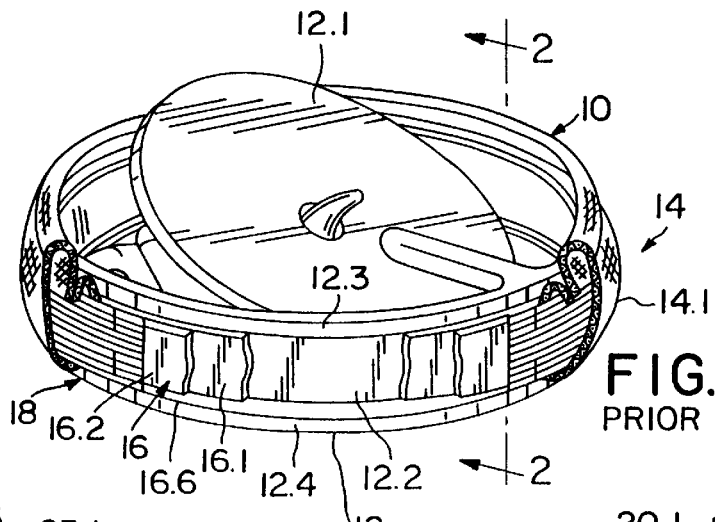
FIG. 1 is a perspective view of a prior art prosthetic heart valve in which the present invention may be implemented.
Figure 2:
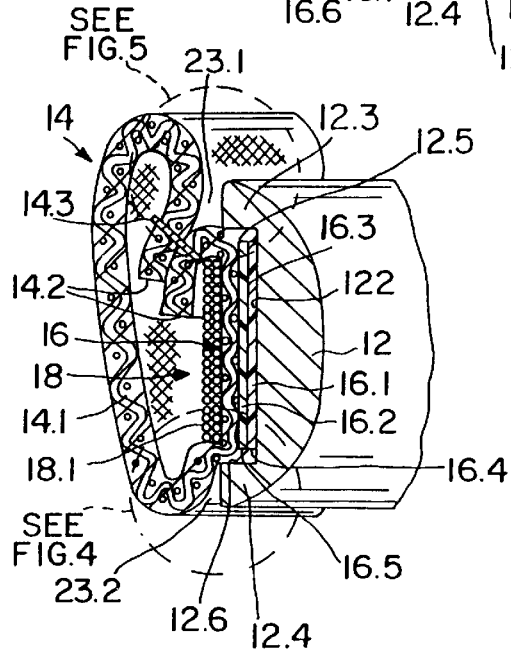
FIG. 2 is a cross-section view of the prior art prosthetic heart valve of FIG. 1 in which the present invention may be implemented.

FIGS. 1 and 2 therefore depict this mechanical heart valve 10 having an annular valve body 12 and an operating valve structure which includes a pivoting disc 12.1 and associated pivots and guides and a suturing ring 14. The annular valve body 12 is desirably rigid, and may be made of titanium, stainless steel, pyrolytic carbon or the like. As depicted in the drawing, the valve body has an exterior annular wall 12.2, the surface of which is desirably generally flat, but which may be concave or convex or of other configuration. Flanges 12.3 and 12.4 extend generally radially outwardly from the valve body at or adjacent to the upper and lower edges of the exterior wall 12.2, respectively. The confronting, generally parallel surfaces 12.5, 12.6 of the flanges 12.3, 12.4 are thus spaced apart a predetermined distance in the direction of flow, and these surfaces, including the wall 12.2, define an annular desirably generally flat-bottomed groove. As mentioned above, it may be desirable in some instances to make the bottom of the groove generally concave or convex, or the groove may have an irregular, wavy surface if desired.

The suturing ring 14 comprises a fabric strip 14.1 made of synthetic fiber, such as polytetrafluoroethylene or polyester of a mesh weave having interstices permeable to tissue ingrowth. The fabric strip 14.1 has longitudinal edges 14.2 which are sewn together to form a seam 14.3, and first and second axial ends sewn together. The strip 14.1 is thereby formed into a torus-shaped or annular shaped ring body having an interior directed minor surface adapted to be fitted against the exterior annular wall of a valve body and an outward directed major surface. As noted below, the torus-shape or annular shape may have any desired cross-section profile, including an elliptical profile, or an irregular profile including a pronounced, flattened upper surface.

The suturing ring 14 may be filled with a biologically acceptable, spongy material, such as silicone rubber or polyurethane or hydrogel and the thus-filled ring may be formed and shaped as desired, two such shapes being shown in the above-referenced '633 and '843 patents. In practice, however, the suturing ring 14 remains unfilled, the fabric thereof being pulled sufficiently tight by the sewing operation as to retain a more or less rounded shape such as that shown in FIGS. 1 and 2.

Slip rings 16 preferably comprise two generally flat polymeric rings with inner ring 16.1 bearing against the annular wall 12.2 between the flanges 12.3, 12.4, and outer ring 16.2 overlying inner ring 16.1. The rings 16.1, 16.2 may be continuous; however, for ease of manufacture, rings 16.1, 16.2 may be formed of narrow, flattened ribbons of polymeric material which can be manually laid about the wall 12.2 with the ends of each ring 16.1, 16.2 being closely adjacent one another or in actual abutting contact. The closely adjacent or abutting ends of the inner ring 16.1 are not aligned with the ends of the outer ring 16.2 so that the ends of the respective rings do not interfere with one another during rotation of the valve body 12 within the suturing ring 14. Other characteristics of the slip rings 16 are described in the above-incorporated '593 patent.

Binding cords 18 are shown in FIGS. 1 and 2 as a series of cord wraps 18.1 overlying the outer ring 16.2. A single cord may be employed to make all of the wraps, or several wraps may be made with each of several cord lengths. The cords 18 desirably are of a heat-relaxable material such as braided polyester. The interstices of the braided cord may be filled with a polymer such as polytetrafluoroethylene. A particularly desirable cord is 2-0 "TEVDEK II", which is a polytetrafluoroethylene impregnated, braided polyester suture sold by the Deknatal Company.

Figure 3:
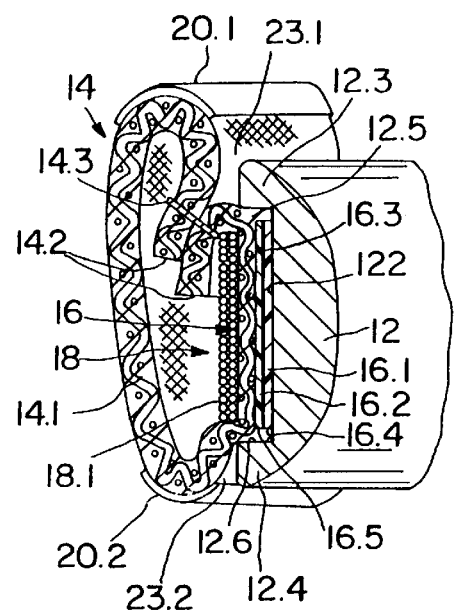
FIG. 3 is a cross-section view of a first embodiment of the present invention effecting an improvement of the prosthetic heart valves of the type depicted in FIGS. 1 and 2.

The first aspect of the invention is depicted in FIG. 3, wherein upper and lower ring shaped area surfaces of the outward directed major surface of suturing ring fabric strip 14.1 are coated with a biocompatible, non-biodegradable polymer such as silicon rubber (polydimethyldiloxane), polyurethane, collagen gel or other appropriate form of biocompatible polymers. The polymer may be dissolved in a solvent, applied by brushing or spraying to the designated areas of the outer surface of the suturing ring in a layer thick enough to close the pores or interstices of the weave of the fabric strip 14.1 and subsequently cured to thereby form impermeable upper and lower coated stripe areas 20.1 and 20.2. In these upper and lower coated stripe areas 20.1 and 20.2, the polymer coating layer seals off the pores or interstices of the mesh weave of the suturing ring fabric strip 14.1, thereby rendering the underlying fabric impermeable, and smoothes the fabric surface topography. The uncoated intermediate band of the fabric strip 14.1 between the upper and lower coated stripe areas 20.1 and 20.2 is intended to be fitted against and sutured to the heart tissue surrounding the tissue orifice where tissue ingrowth is to be encouraged.

After curing, the upper and lower coated stripe areas 20.1 and 20.2 may be grafted with a hydrophilic polymer such as heparin, albumin, polyethylene oxide (or glycol) or other polymers to enhance the blood compatibility. The hydrophilic polymer may also be grafted over the uncoated area of the fabric strip 14.1.

During the healing process after a valve replacement, tissue will grow over the penetrate into the remaining non-polymer coated region of the suturing ring fabric strip 14.1 so that it is anchored to the heart. However, the upper and lower coated stripe areas 20.1 and 20.2 are anticipated to develop only a thin, pseudo-intima type tissue coverage because the initial thrombus deposition on this surface would be much lower. The prospects for pannus overgrowth into the orifice of the prosthetic heart valve 10 is diminished by the barrier presented by the coated stripe areas 20.1 and 20.2.

It will be understood that the widths of the polymer layer coated stripe areas 20.1 and 20.2 are dependent on the cross-section shape of the suturing ring 12. The uncoated band of the fabric strip 14 between the ring shaped polymer layer coated areas 20.1 and 20.2 is intended to be sutured within the prepared heart tissue orifice remaining after removal of the patient's diseased heart valve. Relatively narrow widths of coated areas 20.1 and 20.2 are depicted because the fabric strip 14.1 is itself relatively narrow and makes a relatively tightly rolled suturing ring when fabricated as described above. The invention may also be practiced with the relatively wider, filled suturing ring of the above-referenced '633 patent, incorporated herein by reference. In that case, the suturing ring is wide and relatively flattened in a disk shape to provide an upper flat area that is exposed after the suture ring is sutured into place over and against the heart tissue orifice. The upper coated area 20.1 can accordingly be widened to cover the full exposed area.

Figure 4:
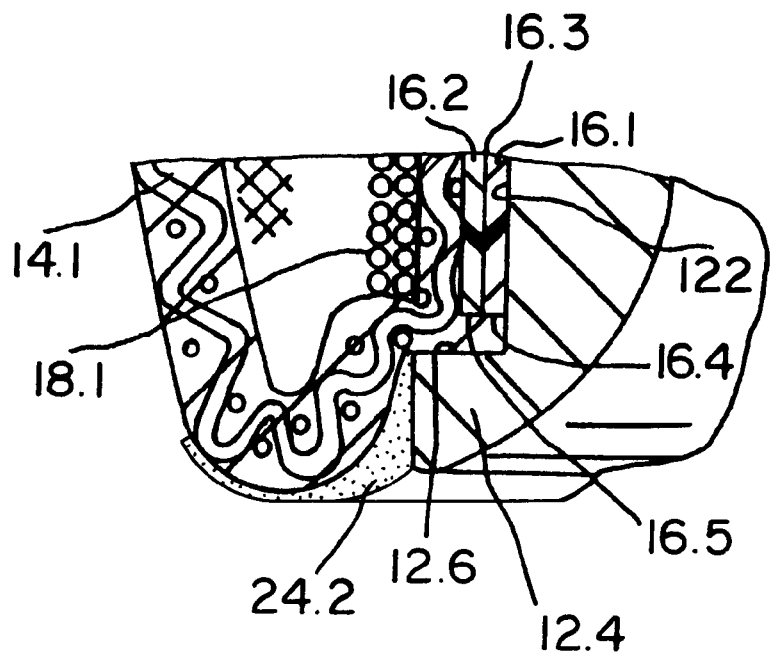
FIG. 4 is a magnified partial cross-section view of FIG. 2 depicting a second embodiment of the present invention effecting an improvement of the prosthetic heart valves of the type depicted in FIGS. 1 and 2.
Figure 5:
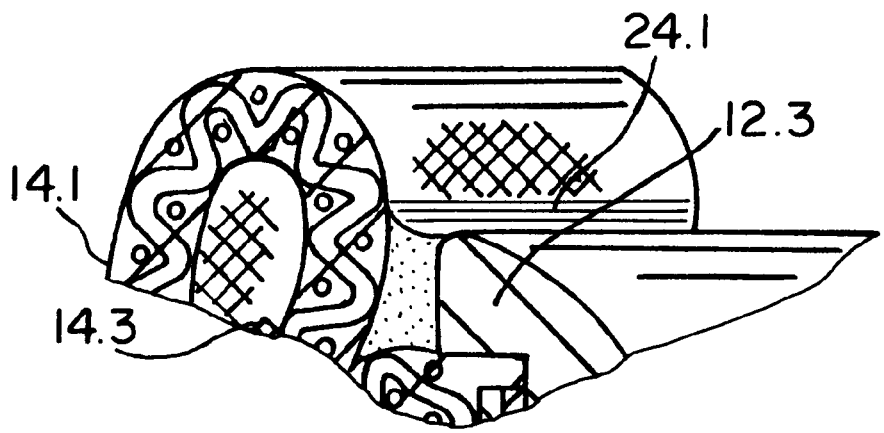
FIG. 5 is a magnified partial cross-section view of FIG. 2 the second embodiment of the present invention effecting an improvement of the prosthetic heart valves of the type depicted in FIGS. 1 and 2.

Turning to FIGS. 4 and 5, they depict an implementation of the second aspect of the invention in the context of the suturing ring configuration of FIGS. 1 and 2. The configuration of this particular suturing ring 14 results in upper and lower annular gaps 23.1 and 23.2 as indicated in FIG. 2. The annular gaps 23.1 and 23.2 appear between the exposed side wall edges of flanges 12.3 and 12.5 and the adjacent outer surfaces of fabric strip 14.1. In accordance with this aspect of the invention, these gaps 23.1 and 23.2 are filled with a flexible, biocompatible polymer of the types described above used for the coated areas 20.1 and 20.2 to form the impermeable smoothing bands 24.1 and 24.2 depicted in FIGS. 4 and 5. The smoothing bands 24.1 and 24.2 may also be wide enough to cover the coated areas 20.1 and 20.2 of FIG. 2. The method described above is used to apply the smoothing bands 24.1, 24.2 in lieu of the coated areas 20.1 and 20.2, although several applying steps may be necessary to fill in the gaps 23.1 and 23.2.

After the smoothing bands 24.1 and 24.2 are formed and dried, they adhere into the interstices of fabric strip 14.1 and to the exposed side wall edges of flanges 12.3 and 12.5. The strength of adherence of the smoothing bands 24.1 and 24.2 to the fabric strip 14.1 exceeds the strength of adherence to the exposed side wall edges of flanges 12.3 and 12.5. Consequently, it is possible to break the bond to the exposed side wall edges of flanges 12.3 and 12.5 by rotation of the suturing ring 14 with respect to the valve body 12.

During the implantation of the heart valve depicted in FIGS. 1–3, a convenient holder attached to the valve body 12 is employed to properly position the suturing ring 14 in a heart tissue orifice which has been prepared to receive the prosthetic valve. The suturing ring 14 is sutured by the surgeon to the heart tissue around the heart tissue orifice. The valve body 12 may then be rotated within the suturing ring 14 as desired by the surgeon so that the valve mechanism may operate without interference from the surrounding tissue. During manual rotation, a counter rotation force is gently applied by the surgeon to the suturing ring 14 to further reduce stresses on the sutured heart tissue. As mentioned above, the torque required for rotation of the valve should be sufficiently small as to avoid rotational forces tending to loosen the sutures or damage the heart tissue which has been sutured to the suturing ring 14, but yet should be sufficiently high as to prevent the valve body from rotating within the suturing ring 14 when heart function has been restored.

During the healing process after a valve replacement, tissue will grow over the penetrate into the remaining non-polymer coated region of the suturing ring fabric strip 14.1 so that it is anchored to the heart. However, the ring shaped polymer layer coated areas 20.1, 20.2 or bands 24.1, 24.2 are anticipated to develop only a thin, pseudo-intima type tissue coverage because the initial thrombus deposition on this surface would be much lower. The prospects for pannus overgrowth into the orifice of the prosthetic heart valve 10 is diminished by the barrier presented by the coated areas 20.1, 20.2 or bands 24.1, 24.2.

While there has been shown what are considered to be the preferred embodiments of the invention, it will be manifest that many changes and modifications may be made therein without departing from the essential spirit of the invention. For example, the stripe areas and gaps may be rendered impermeable or filled by means other than coatings or layers. It is intended, therefore, in the following claims to cover all such changes and modifications as may fall within the true scope of the invention.

We claim:

1. An implantable heart valve having a valve body and an exterior suturing ring for suturing to a natural heart tissue orifice, the valve body having an exterior annular wall with upper and lower edges for receiving the suturing ring disposed circumferentially around the wall, the suturing ring further comprising:

a biocompatible fabric tube of a mesh weave having interstices permeable to tissue ingrowth and first and second axial ends fastened into an annular shaped suturing ring body having an interior directed minor surface and an outward directed major surface adapted to be fitted against the exterior annular;

means for fitting the interior directed surface of the annular shaped suturing ring body against the exterior annular wall leaving the outward directed major surface exposed with an upper ring shaped surface adjacent the upper edge of the valve body and a lower ring shaped surface adjacent the lower edge of the valve body and an intermediate band for being sutured through in attachment of the suturing ring to heart tissue;

a first impermeable layer of biocompatible material over the upper ring shaped surface for filling the interstices of the mesh weave; and a second impermeable layer of biocompatible material over the lower ring shaped surface for filling the interstices of the mesh weave.

2. The heart valve of claim 1 wherein said fitting means further comprises slip ring means interposed between the suturing ring and the wall and circumferential binding means binding the suturing ring and slip ring to the valve body wall, at least one of the binding means and slip ring means being heat-relaxed under controlled conditions to reduce the initial binding force of the binding means to thereby facilitate controlled rotation positioning of the valve body within the suturing ring.

3. The heart valve of claim 2 wherein:

said upper edge of said valve body and said upper ring shaped surface are separated by a first circumferential gap;

said lower edge of said valve body and said upper ring shaped surface are separated by a second circumferential gap;

said first impermeable layer of biocompatible material over the upper ring shaped surface fills said first circumferential gap and the interstices of the mesh weave; and said second impermeable layer of biocompatible material over the lower ring shaped surface fills said second circumferential gap and the interstices of the mesh weave.

4. The heart valve of claim 3 wherein:

said first impermeable layer of biocompatible material over the upper ring shaped surface has a first predetermined width; and said second impermeable layer of biocompatible material over the lower ring shaped surface has a second predetermined width.

5. The heart valve of claim 4 wherein:

said first and second impermeable layers comprise coatings of a biocompatible, non-biodegradable polymer.

6. The heart valve of claim 5 wherein said polymer comprises a selected one of the group consisting of silicon rubber, polyurethane, or collagen gel.

7. The heart valve of claim 1 wherein:

said upper edge of said valve body and said upper ring shaped surface are separated by a first circumferential gap;

said lower edge of said valve body and said upper ring shaped surface are separated by a second circumferential gap;

said first impermeable layer of biocompatible material over the upper ring shaped surface fills said first circumferential gap and the interstices of the mesh weave to provide a smooth transition at the junction of the suturing ring and said upper edge of said valve body; and said second impermeable layer of biocompatible material over the lower ring shaped surface fills said second circumferential gap and the interstices of the mesh weave to provide a smooth transition at the junction of the suturing ring and said lower edge of said valve body.

8. The heart valve of claim 7 wherein:

said first and second impermeable layers comprise coatings of a biocompatible, non-biodegradable polymer.

9. The heart valve of claim 8 wherein said polymer comprises a selected one of the group consisting of silicon rubber, polyurethane, or collagen gel.

10. The heart valve of claim 7 wherein:

said first impermeable layer of biocompatible material over the upper ring shaped surface has a first predetermined width; and said second impermeable layer of biocompatible material over the lower ring shaped surface has a second predetermined width.

11. The heart valve of claim 1 wherein:

said first impermeable layer of biocompatible material over the upper ring shaped surface has a first predetermined width; and said second impermeable layer of biocompatible material over the lower ring shaped surface has a second predetermined width.

12. The heart valve of claim 11 wherein:

said first and second impermeable layers comprise coatings of a biocompatible, non-biodegradable polymer.

13. The heart valve of claim 12 wherein said polymer comprises a selected one of the group consisting of silicon rubber, polyurethane, or collagen gel.

14. An implantable heart valve having a valve body and an exterior suturing ring for suturing to a natural heart tissue orifice, the valve body having an exterior annular wall with upper and lower edges for receiving the suturing ring disposed circumferentially around the wall, the suturing ring further comprising:

a biocompatible fabric tube of a mesh weave having interstices permeable to tissue ingrowth and first and second axial ends fastened into an annular shaped suturing ring body having an interior directed minor surface and an outward directed major surface adapted to be fitted against the exterior annular;

means for fitting the interior directed surface of the annular shaped suturing ring body against the exterior annular wall leaving the outward directed major surface exposed with an upper ring shaped surface adjacent the upper edge of the valve body and a lower ring shaped surface adjacent the lower edge of the valve body and an intermediate band for being sutured through in attachment of the suturing ring to heart tissue; and first means for rendering the upper ring shaped surface impermeable to tissue ingrowth.

15. The heart valve of claim 14 further comprising;

second means for rendering the lower ring shaped surface impermeable to tissue ingrowth.

16. The method of claim 15 wherein:

said first means further comprises a coating over said upper ring shaped surface of a biocompatible, non-biodegradable polymer.

said second means further comprises a coating over said lower ring shaped surface of a biocompatible, non-biodegradable polymer.

17. The heart valve of claim 16 wherein said polymer comprises a selected one of the group consisting of silicon rubber, polyurethane, or collagen gel.

18. The heart valve of claim 15 wherein:

said lower edge of said valve body and said upper ring shaped surface are separated by a second circumferential gap; and said second rendering means comprises a second impermeable layer of biocompatible material over the second ring shaped surface and filling said second circumferential gap to provide a smooth transition at the junction of the suturing ring and said lower edge of said valve body.

19. The heart valve of claim 14 wherein:

said upper edge of said valve body and said upper ring shaped surface are separated by a first circumferential gap; and said first rendering means comprises a first impermeable layer of biocompatible material over the upper ring shaped surface and filling said first circumferential gap to provide a smooth transition at the junction of the suturing ring and said upper edge of said valve body.

20. The heart valve of claim 14 wherein:

said fitting means comprises means separating said upper edge of said valve body and said upper ring shaped surface by a first circumferential gap and separating said lower edge of said valve body and said lower ring shaped surface by a second circumferential gap; and said first rendering means comprises a first impermeable layer of biocompatible material over the upper ring shaped surface and filling said first circumferential gap to provide a smooth transition at the junction of the suturing ring and said upper edge of said valve body; and said second rendering means comprises a second impermeable layer of biocompatible material over the second ring shaped surface and filling said second circumferential gap to provide a smooth transition at the junction of the suturing ring and said lower edge of said valve body.

* * * * *